United States Patent
Robinson et al.

(10) Patent No.: US 9,937,079 B2
(45) Date of Patent: Apr. 10, 2018

(54) MEDICAL DRAPE HAVING AN ULTRA-THIN DRAPE FILM AND A THICK ADHESIVE COATING

(71) Applicant: KCI Licensing, Inc., San Antonio, TX (US)

(72) Inventors: Timothy Mark Robinson, Basingstoke (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 237 days.

(21) Appl. No.: 14/080,285

(22) Filed: Nov. 14, 2013

(65) Prior Publication Data
US 2014/0188059 A1 Jul. 3, 2014

Related U.S. Application Data

(60) Provisional application No. 61/748,400, filed on Jan. 2, 2013.

(51) Int. Cl.
*A61F 13/02* (2006.01)
*A61M 27/00* (2006.01)
(Continued)

(52) U.S. Cl.
CPC .... *A61F 13/0216* (2013.01); *A61F 13/00068* (2013.01); *A61F 13/0233* (2013.01);
(Continued)

(58) Field of Classification Search
CPC ............ A61F 13/00068; A61F 13/0216; A61F 13/0233; A61F 13/0246; A61F 13/0289;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

International Search Report and Written Opinion for corresponding PCT/US2013/070090 dated Mar. 14, 2014.
(Continued)

*Primary Examiner* — Adam Marcetich

(57) ABSTRACT

A system for treating a tissue site includes a pressure source to apply reduced pressure, and a manifold in fluid communication with the pressure source to provide reduced pressure to the tissue site. The system includes a drape for adhering to the tissue site to cover the tissue site and the manifold. The drape has a film layer having a thickness less than about 15 microns, and an adhesive coupled to the film layer. The adhesive seals the film layer to the tissue site to create a sealed space having the manifold therein. The adhesive is sufficiently thick to limit leaks between the film layer and the tissue site.

11 Claims, 3 Drawing Sheets

(51) Int. Cl.
*A61F 13/00* (2006.01)
*A61M 1/00* (2006.01)

(52) U.S. Cl.
CPC ...... *A61F 13/0246* (2013.01); *A61F 13/0289* (2013.01); *A61M 1/0088* (2013.01)

(58) Field of Classification Search
CPC .............. A61F 13/0253; A61F 13/0256; A61F 13/0269; A61F 13/0276; A61F 13/0283; A61F 13/0286; A61M 1/0088; A61B 19/08; A61B 19/088; A61B 2019/084; A61B 2019/085; A61B 17/085; A61B 2019/0201
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,163,448 A * | 11/1992 | Foldesy | A61F 6/04 128/844 |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,469,863 A * | 11/1995 | Shah | A41D 19/0068 128/844 |
| 5,474,783 A * | 12/1995 | Miranda | A61F 13/0276 424/447 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,641,506 A | 6/1997 | Talke et al. | |
| 5,645,081 A | 7/1997 | Argenta et al. | |
| 5,730,994 A * | 3/1998 | Askill | A61L 15/24 424/402 |
| 5,876,745 A * | 3/1999 | Muraoka | A61F 13/0253 424/443 |
| 5,928,972 A * | 7/1999 | Mashiko | A61F 13/0276 442/286 |
| 6,071,267 A | 6/2000 | Zamierowski | |
| 6,135,116 A | 10/2000 | Vogel et al. | |
| 6,241,747 B1 | 6/2001 | Ruff | |
| 6,242,665 B1 * | 6/2001 | Malowaniec | A61F 13/0203 602/41 |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,680,113 B1 * | 1/2004 | Lucast | A61F 13/023 428/343 |
| 6,805,961 B1 | 10/2004 | Watanabe et al. | |
| 6,814,079 B2 | 11/2004 | Heaton et al. | |
| 2002/0077661 A1 | 6/2002 | Saadat | |
| 2002/0106959 A1 * | 8/2002 | Huffines | A61F 13/51458 442/394 |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0208112 A1 * | 11/2003 | Schmidt | A61F 5/443 600/313 |
| 2004/0241215 A1 * | 12/2004 | Lipman | A61F 13/0246 424/445 |
| 2005/0080155 A1 * | 4/2005 | Fattman | A61F 5/443 523/105 |
| 2005/0256251 A1 * | 11/2005 | Amano | C09J 7/0217 524/505 |
| 2006/0057371 A1 * | 3/2006 | Kobayashi | C09J 7/0217 428/355 R |
| 2006/0079852 A1 | 4/2006 | Bubb et al. | |
| 2006/0084735 A1 * | 4/2006 | Takahashi | C09J 7/0217 524/271 |

(56) References Cited

U.S. PATENT DOCUMENTS

| | | | |
|---|---|---|---|
| 2007/0078366 A1* | 4/2007 | Haggstrom | A61F 13/0203 602/53 |
| 2007/0179419 A1 | 8/2007 | Simpson | |
| 2008/0097368 A1* | 4/2008 | Molander | A61F 13/581 604/391 |
| 2009/0105670 A1* | 4/2009 | Bentley | A61F 13/02 604/290 |
| 2009/0234307 A1 | 9/2009 | Vitaris | |
| 2010/0217171 A1* | 8/2010 | Fukano | A61K 8/0208 602/52 |
| 2010/0249733 A9* | 9/2010 | Blott | A61B 17/7092 604/315 |
| 2011/0088624 A1* | 4/2011 | Kenndoff | A61F 13/141 119/14.02 |
| 2011/0098622 A1* | 4/2011 | Hatanaka | A61F 13/0269 602/52 |
| 2011/0129661 A1* | 6/2011 | Tsubaki | C09J 7/0217 428/325 |
| 2011/0152798 A1* | 6/2011 | Eckstein | A61F 13/02 604/319 |
| 2011/0213320 A1 | 9/2011 | Blott et al. | |
| 2011/0282260 A1* | 11/2011 | Kim | A61F 13/02 602/46 |
| 2011/0290259 A1* | 12/2011 | McGuire, Jr. | A61B 19/088 128/849 |
| 2012/0052230 A1 | 3/2012 | Olsson et al. | |
| 2012/0078155 A1* | 3/2012 | Bowman | A61L 15/26 602/54 |
| 2012/0238932 A1* | 9/2012 | Atteia | A61F 13/02 602/52 |
| 2012/0247487 A1* | 10/2012 | Llinas | A61B 17/02 128/849 |
| 2012/0255562 A1* | 10/2012 | McGuire, Jr. | A61B 19/08 128/851 |
| 2013/0090588 A1* | 4/2013 | Buus | A61L 15/585 602/54 |
| 2013/0102947 A1* | 4/2013 | Auguste | A61L 15/225 602/54 |
| 2013/0165838 A1* | 6/2013 | Auguste | A61L 15/225 602/54 |
| 2013/0274696 A1* | 10/2013 | Lam | A61F 5/443 604/332 |
| 2014/0012213 A1* | 1/2014 | Locke | A61F 13/025 604/319 |
| 2014/0046238 A1* | 2/2014 | Leibowitz | A61F 13/00063 602/48 |
| 2014/0248484 A1* | 9/2014 | Bormann | A61F 13/15731 428/220 |
| 2014/0316324 A1* | 10/2014 | Wibaux | C09J 7/0217 602/56 |
| 2015/0290045 A1* | 10/2015 | Fan | A61F 13/00059 602/54 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

(56) References Cited

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
Japanese Office Action corresponding application 2015550385, dated Oct. 3, 2017.

\* cited by examiner

MEDICAL DRAPE HAVING AN ULTRA-THIN DRAPE FILM AND A THICK ADHESIVE COATING

The present invention claims the benefit, under 35 USC § 119(e), of the filing of U.S. Provisional Patent Application Ser. No. 61/748,400, entitled "A Medical Drape having an Ultra-Thin Drape Film and a Thick Adhesive Coating," filed Jan. 2, 2013, by Locke et al., which is incorporated herein by reference for all purposes.

FIELD

The present disclosure relates generally to dressings for adhering to a patient and, more particularly, but not by way of limitation, to a medical drape an ultra-thin drape film with a thick adhesive coating.

BACKGROUND

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative-pressure therapy," "reduced-pressure therapy," or "vacuum therapy") provides a number of benefits, which may include faster healing and increased formulation of granulation tissue. In applying reduced-pressure therapy, typically a foam pad or other manifold is placed proximate to the wound, covered with a drape to form a sealed space, and reduced pressure applied to the sealed space. If the drape leaks, additional energy may be required to overcome the leak and maintain the therapeutic level of reduced pressure.

SUMMARY

These and other problems are generally solved or circumvented, and technical advantages are generally achieved, by embodiments that provide a medical drape formed from an ultra-thin drape layer and a thick adhesive coating.

According to an illustrative, non-limiting embodiment, a system for treating a tissue site is described. The system includes a pressure source to apply reduced pressure, and a manifold in fluid communication with the pressure source to provide reduced pressure to the tissue site. The system also includes a drape for adhering to the tissue site to cover the tissue site and the manifold. The drape has a film layer having a thickness less than about 15 microns, and an adhesive coupled to the film layer. The adhesive seals the film layer to the tissue site to create a sealed space having the manifold therein. The adhesive is sufficiently thick to limit leaks between the film layer and the tissue site.

According to another illustrative embodiment, a dressing for treating a tissue site is disclosed. The dressing includes a connector adapted to receive reduced pressure from a source of reduced pressure and apply the reduced pressure to the tissue site. The dressing also includes a manifold fluidly coupled to the connector for receiving the reduced pressure and having a plurality of flow channels for distributing the reduced pressure to the tissue site. The dressing further includes a drape including a film layer having a thickness less than about 15 microns and an adhesive having a thickness greater than about 80 microns coupled to the film layer to seal the film layer to the tissue site. The drape is configured to cover the tissue site and the manifold to provide a substantially airtight seal that creates a sealed space for the reduced pressure.

According to yet another illustrative embodiment, a method for manufacturing a medical drape is described. The method can provide a film layer having a thickness less than about 15 microns. The method can also apply an adhesive to the first side of the film layer. The method may cure the adhesive to form an adhesive on the first side of the film layer.

According to still another illustrative embodiment, a medical drape having a film layer and an adhesive coupled to the film layer is described. The medical drape may be produced by a process comprising the steps of providing a film layer having a thickness less than about 15 microns. The process may apply an adhesive to the first side of the film layer, and cures the adhesive to form an adhesive on the first side of the film layer.

According to another illustrative embodiment, a medical drape having a film layer and an adhesive coupled to the film layer is described. The film layer may have a thickness less than about 15 microns. The adhesive may have a thickness greater than about 80 microns.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached figures, which are incorporated by reference herein, and wherein.

DETAILED DESCRIPTION OF ILLUSTRATIVE EMBODIMENTS

New and useful systems, methods, and apparatuses associated with medical drapes that may be used with reduced-pressure therapy systems are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

Figure 1:
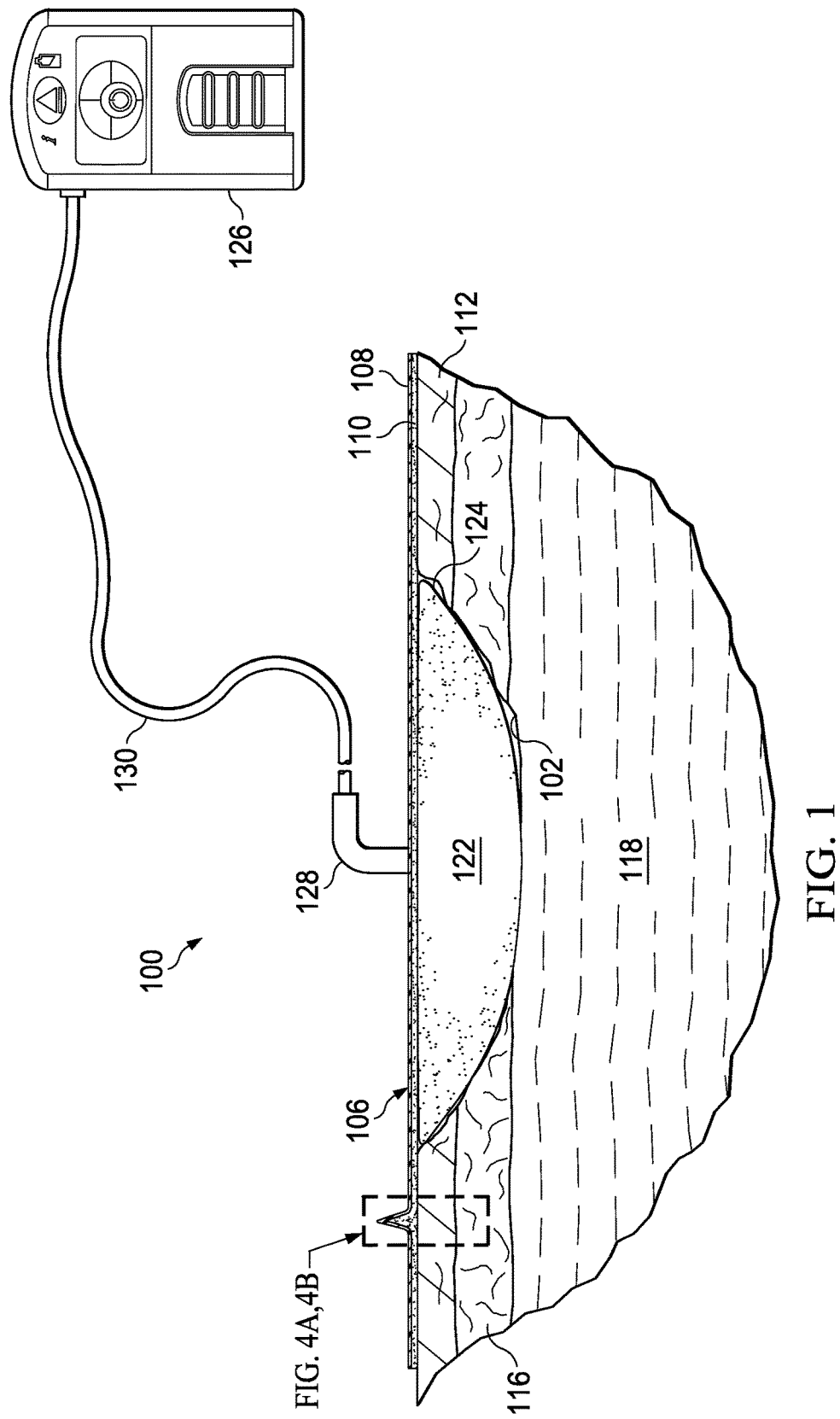
FIG. 1 is a schematic, cross-sectional view with a portion shown in elevation of an illustrative embodiment of a system for treating a tissue site with reduced pressure.

FIG. 1 is a schematic diagram of a reduced-pressure therapy system 100 for treating a tissue site 102 illustrating details that may be associated with some embodiments. The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative-pressure therapy may be used in certain tissue areas to grow additional tissue that may be harvested and transplanted to another tissue location. The tissue site 102 may be a wound that extends through an the epidermis 112, through a dermis 116, and into a subcutaneous tissue 118. The tissue site 102 may include a portion of the epidermis 112 that may be intact and may surround the tissue site 102. Treatment of the tissue site 102 may include removal of fluids, for example, exudate or ascites.

The reduced-pressure therapy system 100 may include a drape 106, a manifold 122, and a connector 128. The drape 106 may have a film layer 108 and an adhesive layer 110 and be disposed over the manifold 122 and the portion of the epidermis 112 surrounding the tissue site 102 to form a sealed therapeutic space 124. The drape 106 may have an aperture permitting fluid communication with the sealed therapeutic space 124 through the drape 106. The manifold 122 may be disposed within the sealed therapeutic space 124 proximate the tissue site 102. The connector 128 may be coupled to the drape 106 and be configured to provide fluid communication through the drape 106 to the sealed therapeutic space 124. The reduced-pressure therapy system 100 may further include a reduced-pressure source 126 and a negative-pressure conduit, such as a tube 130, fluidly coupled to the connector 128.

The manifold 122 may be a substance or structure that may be provided to apply or distribute reduced pressure to the tissue site 102 and also to remove fluids from the tissue site 102. The manifold 122 may include a plurality of flow channels or pathways that can distribute fluids provided to and removed from the tissue site 102 in response to the application of reduced pressure. In one illustrative embodiment, the flow channels or pathways may be interconnected to improve distribution of fluids provided to or removed from the tissue site 102. The manifold 122 may include a biocompatible material that is capable of being placed in contact with the tissue site 102 to distribute reduced pressure to the tissue site 102. The manifold 122 may also be one or more devices that have structural elements arranged to form flow channels. In some illustrative examples, the structural elements may be cellular foam, open-cell foam, porous tissue collections, liquids, gels, and other foams that include, or can be cured to include, flow channels. The manifold 122 may also include porous material, such as foam, gauze, felted mat, or other material suited to a particular biological application. The manifold 122 may further include porous foam that may have a plurality of interconnected cells or pores that act as flow channels. The porous foam of the manifold 122 may be a polyurethane, open-cell, reticulated foam such as GranuFoam® material manufactured by Kinetic Concepts, Incorporated of San Antonio, Tex. In other illustrative embodiments, the manifold 122 may be formed of a bioresorbable material or a scaffold material. In some situations, the manifold 122 may also be used to distribute fluids such as medications, anti-bacterials, growth factors, and various solutions to the tissue site 102.

The reduced-pressure source 126 provides reduced pressure. "Reduced pressure" generally refers to a pressure less than a local ambient pressure, such as the ambient pressure in a local environment external to a sealed therapeutic environment provided by the sealed therapeutic space 124. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The fluid mechanics of using a negative-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

The reduced-pressure source 126 may be a suitable device for supplying reduced pressure, such as a vacuum pump, wall suction, micro-pump, or other source. In an illustrative embodiment, the reduced-pressure source 126 may be an electrically-driven vacuum pump. In another illustrative embodiment, the reduced-pressure source 126 may be a manually-actuated or manually-charged pump that does not require electrical power. Reduced pressure may also be generated by a device, for example, a micro-pump, directly coupled to the drape 106. The reduced-pressure source 126 may be other types of reduced-pressure pumps, or may be a wall suction port such as those available in hospitals and other medical facilities. While the amount and nature of reduced pressure applied to the tissue site 102 may vary according to the application, reduced pressure may be between −5 mm Hg (−667 Pa) and −500 mm Hg (−66.7 kPa), and more typically between −75 mm Hg (−9.9 kPa) and −200 mm Hg (−26.66 kPa).

In general, components of the reduced-pressure therapy system 100 may be coupled directly or indirectly. For example, the reduced-pressure source 126 may be directly coupled to the connector 128 and indirectly coupled to the manifold 122 through the connector 128. Components may be fluidly coupled to each other to provide a path for transferring fluids (i.e., liquid and/or gas) between the components. The connector 128 may also have a port to receive the tube 130 for fluid coupling between the tube 130 and the connector 128. In one illustrative embodiment, the connector 128 may be a T.R.A.C.® Pad or Sensa Pad available from KCI of San Antonio, Tex. The connector 128 may allow reduced pressure to be delivered to the sealed therapeutic space 124. In other illustrative embodiments, the connector 128 may also be a conduit inserted through the drape 106.

A "tube," as used herein, broadly refers to a tube, pipe, hose, conduit, or other structure with one or more lumina adapted to convey fluids between two ends. Typically, a tube may be an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, pneumatic, thermal, electrical, or chemical coupling (such as a chemical bond) in some contexts. For example, the tube 130 may be a multi-lumen conduit having a primary lumen and a secondary lumen. In an illustrative embodiment, the tube 130 may supply reduced pressure through the primary lumen and may sense pressure through the secondary lumen. The tube 130 may have a variety of shapes and include multiple primary and secondary lumens. The tube 130 may fluidly communicate with the sealed therapeutic space 124 through the connector 128 to supply the sealed therapeutic space 124 with reduced pressure and sense pressure at the tissue site 102. Reduced pressure developed by the reduced-pressure source 126 may be delivered through the tube 130 to the connector 128.

In general, exudates and other fluids flow toward lower pressure along a fluid path, a phenomenon often referred to as "suction" or "vacuum." This orientation may be generally presumed for purposes of describing various features and components of reduced-pressure therapy systems herein. Thus, the term "downstream" typically implies something in a fluid path relatively closer to a negative-pressure source, and conversely, the term "upstream" implies something relatively further away from a negative-pressure source. Similarly, it may be convenient to describe certain features in terms of fluid "inlet" or "outlet" in such a frame of reference. However, the fluid path may also be reversed in some applications (such as by substituting a positive-pressure source for a negative-pressure source) and this descriptive convention should not be construed as a limiting convention.

In general, negative-pressure therapy can be beneficial for wounds of all severity, but the cost and complexity of negative-pressure therapy systems often limit the application of reduced-pressure therapy to large, highly-exudating wounds present on patients undergoing acute or chronic care, as well as other severe wounds that are not readily susceptible to healing without application of reduced pressure. For example, the complexity of conventional negative-pressure therapy systems can limit the ability of a person with little or no specialized knowledge from administering negative-pressure therapy.

Often, the effectiveness of negative-pressure therapy may be limited due to the inability of the drape 106 to conform to the tissue site 102 while still providing a seal between the drape 106 and the epidermis 112. Polyurethane films may often be used to form the film layer 108 of the drape 106 due to polyurethane's ability to be breathable, flexible, robust, printed or colored, and provided in a range of thicknesses. Polyurethane film layers also bond well to most adhesives. The challenges for using polyurethane films in medical drape applications is to balance between conformability, adhesion, sealing, breathability, robustness, and cost. Currently, most medical drapes have film layers with a thickness ranging from at least 15 microns to about 50 microns. Such medical drapes may be manufactured by starting with a polyurethane film layer having a thickness of about 5 microns. A polyurethane film having a thickness of about 5 microns may not be considered a medical grade material. Typically, a polyurethane film having a thickness of about 5 microns may be used as an intermediary stage of the manufacturing process. The polyurethane film layer may be further coated with other polyurethane solutions to achieve a final thickness of 15 microns or more. The 5 micron film layer is not currently available for medical applications for a variety of reasons that will be discussed below, but only used in the manufacturing process.

The medical drape functions to enclose and protect the wound, maintain a moist environment within the wound, act as a barrier to infectious agents, and provide a seal, particularly where reduced-pressure therapy is being utilized. When low-leak or no-leak reduced-pressure therapies are used, the ability of the medical drape to seal the tissue site and maintain the reduced pressure at a desired level becomes more critical. In order to improve sealing of a medical drape, a thicker adhesive may be required. The adhesive, commonly acrylic-based, may have a coating coverage between about 15 $g/m^2$ (gsm) up to about 65 gsm which equates to a coating thickness ranging between about 15 microns and about 65 microns for medical applications. It is understood that the thicker adhesives, that is, adhesives having a thickness closer to about 65 microns, combined with a polyurethane film layer having a standard thickness of 15 microns or more to form a medical drape may be useful for such low-leak or no-leak reduced-pressure applications.

Figure 4A:
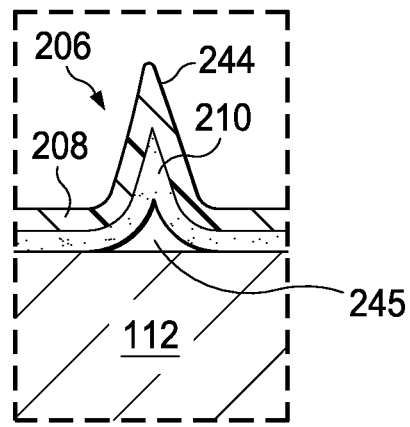
FIG. 4A is a detail in cross section of a portion of the system of FIG. 1 with another medical drape.

However, medical drapes having a thicker adhesive layer may have an increased size and an increased structural complexity that may give rise to increased manufacturing costs. Medical drapes having a thicker adhesive may also negatively effect conformability and breathability. To overcome these problems, a medical drape may have a thinner polyurethane film layer. For example, a polyurethane film layer approximately 10 microns or less may be used. However, polyurethane films having a thickness of approximately 10 microns or less may be prone to stretching, creasing or wrinkling, and tearing during manufacturing. The creases or wrinkles may create leakage problems. For example, FIG. 4A is a sectional view of a drape 206 illustrating additional details of a medical drape having a thinner polyurethane film layer and thicker than standard adhesive layer. The drape 206 may be formed from a polyurethane the film layer 208 having a thickness of greater than about 15 microns and an the adhesive 210 less than about 80 microns is shown. When the drape 206 is positioned at the tissue site 102 over the manifold 112, a crease 244 is formed leaving a gap 245 because the adhesive 210 is too thin to seal the gap 245.

Efforts to use thinner polyurethane films less than about 15 microns have also not resolved the problems because such film layers, especially those having a thickness of about 5 microns, may be susceptible to the risk of pin-holing defects. Pin-holing is the forming of microscopic openings or tears in the flexible film that may cause the film layer, and consequently the medical drape, to fail. In addition, the polyurethane film thickness must be maintained to aid in handling of the medical drape as thinner polyurethane films may make the medical drape more difficult to apply. It is also known that some adhesives, such as acrylic adhesives, significantly reduce the moisture vapor transmission rate (MVTR) of a medical drape as the adhesive layer increases in thickness. Because of these problems, polyurethane film layers having a thickness of 5 microns have not been available for medical drape applications especially for low-leak or no-leak applications of reduced-pressure therapy. Because of the unavailability of such thin film layer polyurethane, the adhesive layer has remained relatively thin, between approximately 15 microns and approximately 65 microns, to maintain an acceptable MVTR.

As disclosed herein, system 100 overcomes these challenges and others by providing a drape 106 having a thinner the film layer 108 and a thicker the adhesive 110. In addition, the drape 106 may provide a thicker adhesive without compromising breathability or conformability. Still further, the drape 106 having a thinner film layer may be less susceptible to pin-holing defects.

Figure 2:
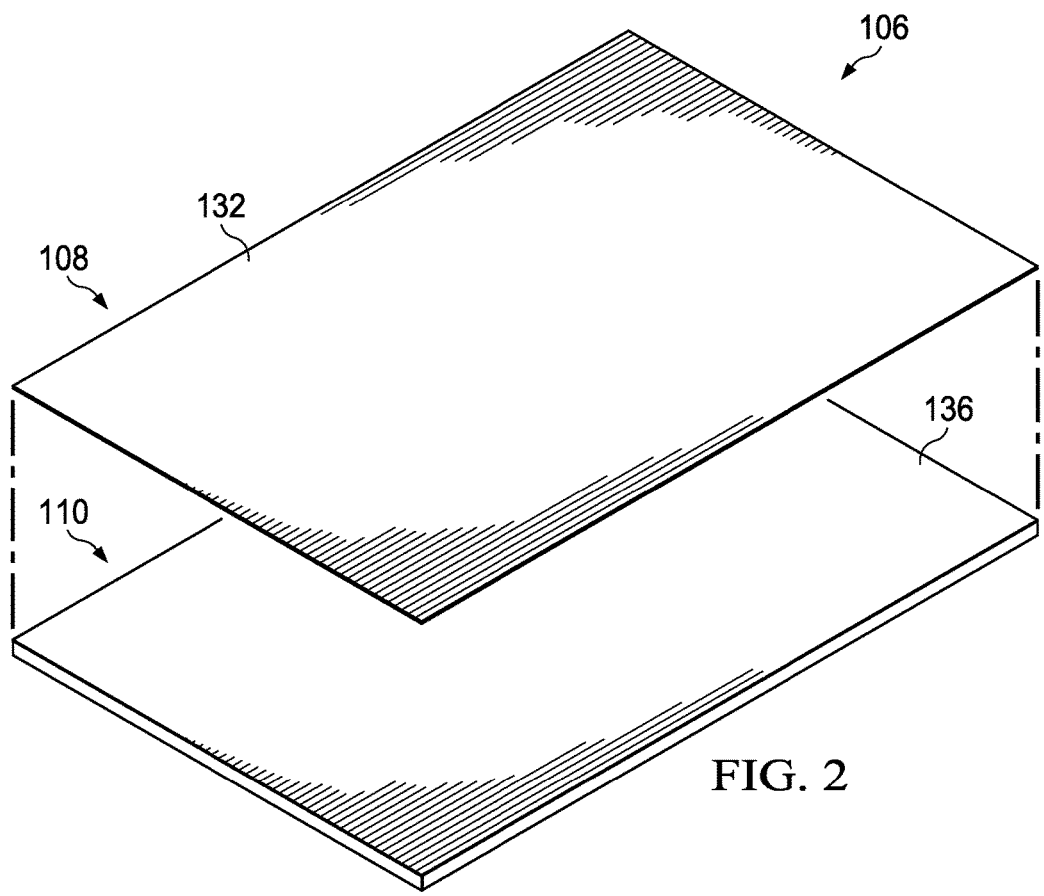
FIG. 2 is an exploded, perspective view of an illustrative embodiment of a medical drape of FIG. 1.
Figure 3:
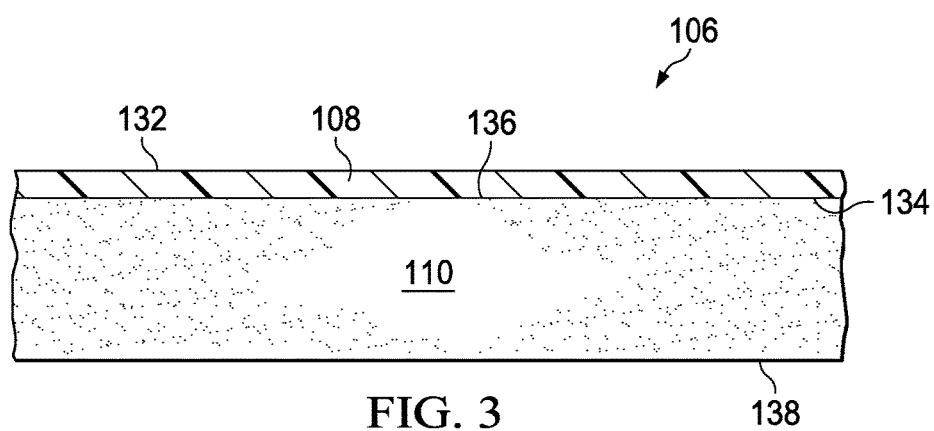
FIG. 3 is a cross-sectional view of a portion of the medical drape of FIG. 2.

FIG. 2 is an exploded perspective view of the drape 106 illustrating additional details that may be associated with some embodiments. The drape 106 may include the film layer 108 and the adhesive layer 110. The adhesive 110 may be configured to be positioned adjacent to the film layer 108. The film layer 108 may have a first side 132 and a second side 134. The first side 132 may be configured to be non-tacky so that the first side 132 may not generally adhere to objects placed in contact with the first side 132. The film layer 108 may also be configured to be an exterior or upper portion of the drape 106 so that the first side 132 may be exposed to the ambient environment when positioned at the tissue site 102. The adhesive 110 may have a first side 136 configured to be coupled to the film layer 108 and a second side 138 configured to be coupled to the epidermis 112. The adhesive 110 may be a material that both bonds and seals the film layer 108 of the drape 106 to a portion of the epidermis 112 surrounding the tissue site 102 whereby the drape 106 forms sealed space 124 when disposed over the tissue site 102.

The drape 106 substantially prevents the leakage of fluids, for example, through the space between the drape 106 and the tissue site 102, while allowing vapor to egress through the drape 106. The drape 106 may maintain a suitable MVTR where the adhesive 110 contacts the epidermis 112 to aid in healing of the tissue site 102 and limit maceration of the epidermis 112 to which the drape 106 is sealed. The drape 106 may also maintain sealing contact with the epidermis 112 surrounding the tissue site 102 when the reduced-pressure therapy is applied to the tissue site 102. The drape 106 also may be formed from a material that is suitably releasable from the epidermis 112 to minimize or reduce pain to the patient resulting from the removal of the drape 106 from the tissue site 102. While the drape 106 may be releasable, the drape 106 maintains an adequately strong mechanical connection to the tissue site 102 as a function of the bonding characteristics of the adhesive 110.

The film layer 108 may be a flexible film that may be breathable and typically may have a high moisture-vapor-transfer-rate (MVTR). The film layer 108 may be formed from a range of medically approved films ranging in thickness of less than about 5 microns. The film layer 108 may comprise a suitable material or materials, such as the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. The high MVTR of the film layer 108 allows vapor to egress and inhibits liquids from exiting. In an illustrative embodiment, the film layer 108 may also function as a barrier to liquids and microorganisms.

The adhesive 110 may be a medically-acceptable, pressure-sensitive adhesive. In an illustrative embodiment, the adhesive 110 may be a high bond strength acrylic adhesive, high-tack silicone adhesive, polyurethane, or other substance. In some embodiments, the bond strength of the adhesive 110 may have a peel adhesion or resistance to being peeled from a stainless steel material between about 6N/25 mm to about 10N/25 mm on stainless steel substrate at 23° C. at 50% relative humidity based on the American Society for Testing and Materials ("ASTM") standard ASTM D3330. In an illustrative embodiment, the adhesive 110 comprises an acrylic adhesive with a coating weight between about 80 gsm and about 400 gsm. A coating weight between about 80 gsm and about 400 gsm may correspond to a thickness of about 80 microns to about 400 microns. In other embodiments, the adhesive 110 may be a silicone adhesive with a coating weight of up to 600 gsm. In still other embodiments, the adhesive 110 may be a hydrocolloid adhesive having a coating weight of up to 1000 gsm.

The drape 106 having the adhesive 110 may be manufactured using a hot melt manufacturing system. The drape 106 may also be manufactured using a manufacturing process that does not use a solvent coating system as currently known in the art. Hot melt manufacturing systems melt the adhesive of the adhesive 110 so that the adhesive becomes less viscous. The melted adhesive may then be applied to the film layer 108 and cooled to form the adhesive 110. In an illustrative embodiment, a film layer having a thickness less than about 15 microns may be provided. The acrylic adhesive of the adhesive 110 may be heated up to about 120° C. to melt the acrylic adhesive of the adhesive 110. Other adhesives may be heated to higher or lower temperatures to achieve a suitable viscosity for application of the particular adhesive to the film layer 108. The melted adhesive may be applied to the film layer 108 and cured to form the adhesive 110. In an illustrative embodiment, the melted adhesive may be coated onto the film layer 108 and cooled to form the adhesive 110. The drape 106 may also be manufactured in an extrusion process to pattern coat the film layer 108 with the adhesive 110 so that the adhesive 110 may have different thicknesses at different portions of the drape 106.

The drape 106 may be susceptible to fewer instances of pin-holing than expected when limiting the film layer 108 to a thickness of less than 15 microns. The increased thickness of the adhesive 110 may decrease the instances of pin-holing by filling the pin-holes that form in the film layer 108. In addition, the overall breathability of the drape 106 may be increased over other medical drapes because of the improved MVTR of the film layer 108. Increasing the thickness of the adhesive of the adhesive 110 may decrease the MVTR of the adhesive 110, but reducing the thickness of the film layer 108 increases the MVTR of the film layer 108 to balance out the lower MVTR of the adhesive 110. Pairing the adhesive 110 with the film layer 108 may cause an increase in the overall MVTR of the drape 106 or at least maintain the overall MVTR at an acceptable level, aiding in maintenance of healthy the epidermis 112 adjacent the tissue site 102.

As described above, FIG. 4A is a cross sectional view of a portion of system 100 of FIG. 1 using a common medical the drape 206 having a film layer 208 between about 25 microns and about 45 microns and an the adhesive 210. When medical the drape 206 is applied to the tissue site 102, medical the drape 206 may be stretched to conform medical the drape 206 to the tissue site 102 and ensure that medical the drape 206 seals to the intact the epidermis 112 surrounding the tissue site 102. When the force stretching medical the drape 206 during application is released, medical the drape 206 may contract, causing wrinkle or the crease 244 to form where medical the drape 206 is coupled to the epidermis 112. The crease 244 pulls both the film layer 208 and the adhesive 210 away from the epidermis 112, and due to the thickness of the film layer 208, the adhesive 210 is not sufficiently strong or thick enough to close the gap between medical the drape 206 and the epidermis 112. Thus, the crease 244 causes leaks that reduce the efficiency of system 100.

Figure 4B:
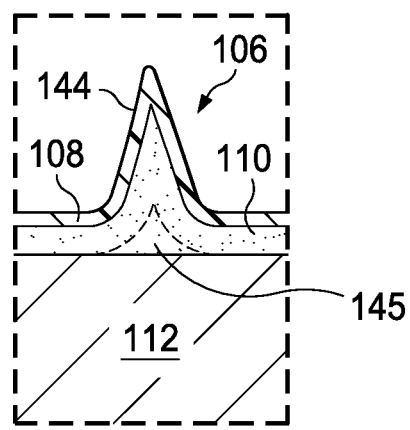
FIG. 4B is a detail in cross section of the portion of the system of FIG. 4A with the medical drape of FIG. 3.

FIG. 4B is a cross sectional view of a portion of system 100 of FIG. 1 illustrating additional details of the drape 106 that may be associated with some embodiments. The drape 106 may be less than about 15 microns, but still include wrinkle or the crease 144. The crease 144 may cause a portion of the drape 106 to be pulled away from the epidermis 112 as described above. However, because the adhesive 110 may be thicker, between about 80 microns and 400 microns, the adhesive 110 may not pull away from the epidermis 112 to form a gap 145 as shown by the dashed line. The adhesive 110 may fill the entire void under the crease 144, preventing a leak. The adhesive 110 may fill the openings between the film layer 108 and the epidermis 112, thereby limiting the formation of leaks that may prevent proper operation of system 100. Thus, the drape 106, substantially prevents leakage of fluid through the space between the drape 106 and the tissue site 102, while maintaining a high MVTR and increased conformability.

In other embodiments, the adhesives may be mixed with blowing or expanding agents, for example organic and inorganic low temperature boiling point liquids. The blowing or expanding agents allow for the adhesives to expand under the application of heat or light to increase the thickness of the adhesive following deposition by one of the above described processes. The blowing or expanding agents may reduce the amount of adhesive needed and decrease the cost of production and the cost of the resulting medical drape. In some embodiments, the application of heat or light may be delayed until application of the medical drape to the epidermis so that the contact area with the epidermis increases as the adhesive may be warmed by contact with the epidermis. The application of light or heat following application of the medical drape to the epidermis may provide a better seal of the medical drape to the epidermis while retaining strong bonding characteristics.

The medical drapes and their equivalents as described above may be thinner than standard drapes, may have high MVTRs, and may be highly conformable. In addition, they may have reduced instances of leaks due to their increase adhesive thickness. Still further the medical drapes and their equivalents described herein may have a lower production cost. The medical drapes and their equivalents herein may also be subject to simpler application and high breathability.

Although the certain embodiments and their advantages have been disclosed in the context of certain illustrative, non-limiting embodiments, it should be understood that various changes, substitutions, permutations, and alterations can be made without departing from the scope of the invention as defined by the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate and as otherwise understood by one skilled in the art.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A system for treating a tissue site, the system comprising:
    a pressure source configured to apply reduced pressure;
    a manifold adapted to be in fluid communication with the pressure source to provide reduced pressure to the tissue site; and
    a drape comprising:
        a film layer having a thickness less than 5 microns,
        an adhesive coupled to the film layer and adapted to seal the drape over the manifold and the tissue site to create a sealed space with the manifold therein, and
        the adhesive having a thickness greater than about 80 microns and less than about 200 microns to limit leaks between the film layer and the tissue site, wherein the adhesive is configured to limit leaks through the drape if a pin-hole opening forms in the film layer.

2. The system of claim 1, wherein the film layer is a polyurethane.

3. The system of claim 1, wherein the adhesive is a silicone adhesive.

4. The system of claim 1, wherein the adhesive is an acrylic adhesive and the film layer is a polyurethane.

5. A dressing for treating a tissue site, the dressing comprising:
    a connector adapted to receive reduced pressure from a reduced-pressure source and apply the reduced pressure to the tissue site;
    a manifold adapted to be fluidly coupled to the connector for receiving the reduced pressure and having a plurality of flow channels for distributing the reduced pressure to the tissue site; and
    a drape the drape including a film layer having a thickness less than 5 microns and an adhesive coupled to the film layer and configured to seal the film layer to the tissue site, the adhesive having a thickness greater than 200 microns and less than 300 microns and a bond strength between about 6N/25 mm and about 10N/25 mm, wherein the adhesive is configured to limit leaks through the drape if a pin-hole opening forms in the film layer.

6. The dressing of claim 5, wherein the film layer is a polyurethane.

7. The dressing of claim 5, wherein the adhesive is a silicone adhesive.

8. The dressing of claim 5, wherein the adhesive is an acrylic adhesive.

9. The dressing of claim 5, wherein the adhesive is an acrylic adhesive and the film layer is a polyurethane.

10. The dressing of claim 5, wherein the adhesive comprises a hydrocolloid adhesive.

11. The dressing of claim 5, wherein the thickness of the adhesive at a first portion of the drape is different than the thickness of the adhesive at a second portion of the drape.

* * * * *